United States Patent [19]

Van Moerkerken

[11] Patent Number: 5,767,157

[45] Date of Patent: Jun. 16, 1998

[54] ARTHRITIC PAIN PREVENTION METHOD AND COMPOSITIONS

[76] Inventor: Arthur Van Moerkerken, 18761 West Dixie Hwy., #209, North Miami Beach, Fla. 33180

[21] Appl. No.: 587,212

[22] Filed: Jan. 16, 1996

[51] Int. Cl.$^6$ ............................................. A61K 31/195
[52] U.S. Cl. ........................... 514/562; 514/564; 514/565
[58] Field of Search ................................. 514/564, 562, 514/565

[56] References Cited

PUBLICATIONS

Budavari, ed., The Merck Index, eleventh edition, entry 6826 "Ornithine", p. 1086, 1989.

Primary Examiner—William R. A. Jarvis

[57] ABSTRACT

Disclosed is the method of determining the effectiveness of an agent for the prevention of pain in a person's joints, comprising the steps of a) administering to a susceptible subject a quantity of a trigger substance reproducibly effective in producing within a period of not more than ten hours the occurrence of pain in a joint of said subject lasting for at least one week in the absence of treatment, b) administering to said subject having received said quantity of trigger substance a predetermined quantity of the agent whose effectiveness is to be determined, c) measuring the time required for relief of pain in a joint of the subject upon administering said agent, and d) comparing the time required for relief of said pain with and without the administration of said agent. Also disclosed are effective quantities of certain nutrient substances which can reproducibly relieve pain in a joint produced in a susceptible subject by the administration of a trigger substance.

10 Claims, No Drawings

1

ARTHRITIC PAIN PREVENTION METHOD AND COMPOSITIONS

This invention relates to the relief and prevention of pain in one or more of a person's joints. More particularly, this invention relates to the relief and prevention of pain associated with those musculosketal disorders that primarily affect the joints. Joint disorders are further classified into the periarticular tissue disorders (eg tennis elbow) and the true articular or joint diseases (eg osteoarthritis). The MERCK MANUAL, 16th edition, published 1992, at pages 1297 to 1300, which portion is here incorporated by reference, contains a table titled "Classification of the Rheumatic Diseases" that includes ten major categories of disease including among others Diffuse Connective Tissue Diseases embracing rheumatoid arthritis and 17 other diseases and conditions; Arthritis associated with Spondylitis embracing 5 diseases and conditions; two kinds of Osteoarthritis; and 13 kinds of Arthritis, Tenosynovitis, and Bursitis associated with infectious agents. Most of these diseases and conditions are accompanied by pain. As pointed out by this publication, "we do not yet fully understand the causes of nor can we completely control joint pain."

Also according to this reference, a few types of arthritis are treatable with specific therapy; for example, gout can be completely controlled with drugs, or Lyme disease can be treated with antibiotics, but there are no "magic bullets" for most chronic rheumatic disorders. Optimal management for patients with severe musculoskeletal disease requires many skills and resources and the collaboration of rheumatologists, orthopedic surgeons, paramedical specialists, and support services. Drug therapy is synergistic to other treament in providing symptomatic control and suppression of disease and rarely should be relied alone. Disease suppression can be achieved with hypouricemic drugs for gout, corticosteroids and immunosuppressive agents for immunologic and inflammatory diseases, and a range of miscellaneous slow-acting drugs for rheumatoid arthritis and the arthropathies associated with spondylitis. Aspirin has been used for pain and inflammation since early in this century. More recent drug therapy for rheumatoid arthritis includes gold injections, penicillamine, hydroxychloroquine, and sulfasalazine. However, drug control of these conditions remains imperfect, and better understanding and new approaches are urgently needed.

For rheumatoid arthritis in particular, the same reference notes that among nonsteroidal anti-inflammatory drugs (NSAIDs), salicylates are relatively safe, inexpensive, analgesic, and anti-inflammatory, and are the traditional cornerstone of drug therapy in rheumatoid arthritis. Aspirin is begun with 600 to 1000 milligrams four times daily and adjusted upward until achieving a maximally effective or mildly toxic dose (eg tinnitus, diminished hearing) to a final dose from 3000 to 6500 milligrams per day. Other NSAIDs are available for patients who do not tolerate suficient aspirin to obtain a good effect, as shown in the following table:

| Agent | Recommended dosage |
| --- | --- |
| Indomethacin | 25 milligrms three or four times daily |
| Ibuprofen | 400–800 mg four times daily |
| Naproxen | 250 mg twice daily or up to 1250 mg/day |
| Fenoprofen | 300–600 mg four times daily, 3200 mg maximum |
| Tolmetin | 400 mg three times daily, 2000 mg maximum |
| Sulindac | 150–200 mg twice daily |

-continued

| Agent | Recommended dosage |
| --- | --- |
| Meclofenamate | 200–400 mg/day |
| Ketoprofen | 150–300 mg/day |
| Proxicam | 20 mg once daily |
| Flurbiprofen | 100 mg twice or three times daily |
| Diclofenac | 75 mg twice daily or 50 mg four times daily |

While less irritating to the gastrointestinal tract than aspirin, these NSAIDs can also produce gastric symptoms and bleeding.

Gold and the other slowly acting drugs are considered for use when aspirin or other NSAIDs are not sufficiently beneficial after 3 to 4 months of treatment. These drugs, too, are unfortunately subject to toxic side effects.

Corticosteroids are the most dramatically effective short-term anti-inflammatory drugs, but rheumatoid arthritis is usually active for years, and clinical benefit from corticosteroids often diminishes with time.

As pointed out by W. Michne (Encyclopedia of Chemical Technology, third edition, vol. 2, pages 574–586), "the search for new, more effective analgesics and anti-inflammatory agents with fewer and/or less severe side effects is a continual endeavor, and promising agents are ultimately (emphasis added) studied in man. The laboratory and clinical evaluations of new drugs are complex disciplines . . . " The writer implies that before a "promising agent" is studied in man, it must be established by testing with animals that administration to humans is safe, and that the agent offers at least some promise of mitigating human pain. While methods of evaluating safety are well known, study of analgesic effectiveness in experimental animals is not straightforward and remains a controversial subject, especially with respect to correlation of effects in animals and in humans.

J K Saelens and F R Granat ("New Drug Discovery and Development", pages 263-)have described a "phenylquinone writhing test in mice" that is sensitive to all known analgesics and therefore deemed an excellent primary screening test for new candidates. Male mice receive intraperitoneally 0.1 ml/10 g body weight of an 0.25 mg/ml solution of phenyl-p-quinone in 5% aqueous ethanol. Five minutes later they are placed in observation cages and the number of animals which do not perform a characteristic writhe during the next 10 minutes are recorded. The authors found that phenylquinone induces one or more writhes in 95% of the injected mice. Test compounds are then administered and evaluated for their effectiveness in inhibiting the characteristic writhe response to phenylquinone.

While this is only one test method of many that have been proposed, it serves to illustrate the laboriousness and complexity of the effort required. Yet this effort is merely that of one stage in the process, i.e. that of the primary screening for activity. For an overview of the entire process from the proposal of an idea by a researcher to the initiation of clinical trials of a remedy, reference can be had to "Natural History of a Typical Drug" a chapter by Dr. E. L. Harris in "The Principles and Practice of Clinical Trials" (Harris and Fitzgerald, editors, E. & S. Livingstone, Edinburgh and London, 1970). Harris writes "The first stage is that of the idea. Whatever the source of the idea, it is considered by a research panel consisting of medical, chemical, pharmacological, pharmaceutical and commercial interests. If the panel feel that the idea has merit, then the research chemist sets about synthesising the compound or a number of related compounds. This can be a very long and arduous task; it has been estimated that synthesis and initial biological screening of a single compound can take up to 400 man hours to achieve....

When sufficient quantities have been made the pure drugs are handed over to the pharmacologist who carries out a programme of empirical screening tests, designed to cover as wide a range of pharmacological actions as economically as possible so as to expose any effects which might be of therapeutic use. If an action is detected more detailed experiments to elucidate this are carried out.

Many compounds are rejected at this stage either because of lack of activity or gross toxicity. Those that do survive are again considered by the research panel who decide whether the agent has sufficient promise to go forward to assess its safety in animals.

There are three phases in toxicity testing. The first is the acute toxicity study which deals with the quantitative assessment of the short term effects of a drug. The response is noted after a single oral or parenteral dose, or several doses given within 24 hours. These tests are carried out in a variety of species.

The next is sub-acute toxicity, and in general covers repeated dosage in at least two species, such as mice and rats, for periods up to 90 days. An additional non-rodent species, eg. dog, is often included.

Chronic studies are for the duration of life in the animal—rats and mice are suitable. Occasionally long term studies are employed in other animals such as dogs and monkeys for periods up to two years....

When the exacting toxicological studies are completed and the research panel is satisfied with all the data that has been generated, the drug is administered to healthy volunteers..."

Application of these and similar methods has led to a number of successful products in the field of major analgesics, i.e. substances that mimic the pain relieving effectiveness of morphine with reduced tendency to physical dependence. However, there have been fewer successes in the field of the NSAIDs and other drugs effective against joint disease related pain.

L F Meisner U.S. Pat. No. 4,772,591 of Sep. 20, 1988 disclosesd accelerating the healing of wounds by administration of a composition comprising a mild anti-inflammatory agent and substances which in combination have been found to accelerate fibrous tissue growth and scar tissue formation. Meisner's method comprises the administration of four substances: a source of biologically available calcium, ascorbic acid, a precursor or stimulant of epinephrine or nor-epinephrine production selected from among tyrosine and phenylalanine, and a mild anti-inflammatory substance selected from the anti-inflammatory members of the group consisting of simple sugars, amino sugars, amino acids, and derivatives thereof. The preferred member of this anti-inflammatory group is glucosamine; specifically listed anti-inflammatory amino acids are cysteine, creatine, creatinine, L-tryptophan, valine, alanine, glycine, glutamine, aspartic acid, and S-methylcysteine.

Clearly, in this field there remains a need for improved agents as well as improved techniques for their discovery.

SUMMARY OF THE INVENTION

In accordance with this invention, I have found that I can reproducibly cause a susceptible human subject to experience perceptible pain in a joint within a short period of time upon the oral administration of a sufficient quantity of any of a class of substances which I propose to call trigger substances. These trigger substances are in widespread consumer use and are without specific effect on the great majority of the human population. In a susceptible subject, however, the effect is both reproducible and sufficiently long lasting to serve as research tool for the evaluation of agents effective in relieving pain in a joint. Accordingly, the method of determining the effectiveness of an agent for relieving pain in a joint of a person in need of such relief, comprises the steps of a) administering to a susceptible subject a quantity of a trigger substance reproducibly effective in producing within a period of ten days or less the occurrence of pain in a joint of said subject lasting for at least one week in the absence of treatment, b) administering to said subject having received said quantity of trigger substance a predetermined quantity of the agent whose effectiveness is to be determined, c) measuring the time required for relief of pain in a joint of the subject upon administering said agent, and d) comparing the time required for relief of said pain with and without the administration of said agent.

An effective agent in accordance with this invention, therefore, is one that when so administered results in the person receiving said agent experiencing relief of pain in a joint in less time than in the absence of such agent.

Also in accordance with this invention, I have found that effective quantities of certain nutrient substances can reproducibly relieve pain in a joint produced in a susceptible subject by the administration of a trigger substance in less time than required by a non-steroidal anti-inflammatory remedy such as aspirin. Such nutrient substances, which are ingested and metabolized by humans daily, are inherently safe. Accordingly, the method of relieving pain in a joint of a person in need of such relief, comprises the administration to such person of a quantity of an agent determined to be effective in relieving pain by the method of this invention. Such administration of an agent can take place after the administration of a trigger substance, at the same time as a trigger substance is administered, or even before a trigger substance is administered, so that the sensation of pain in a joint that would be produced without the agent is thereby prevented.

Also in accordance with this invention, I have found that an agent found effective in accordance with this invention in relieving pain can be combined with a pharmaceutically acceptable carrier to provide an effective palatable composition for the relief and prevention of pain in a joint. Moreover, I have found that a combination of two or more selected agents found effective in accordance with this invention in relieving pain can be combined with a pharmaceutically acceptable carrier to provide a pleasant tasting as well as effective and palatable composition for the relief and prevention of pain in a joint.

DESCRIPTION OF PREFERRED EMBODIMENTS

Trigger Substances:

A trigger substance according to this invention is defined as any substance that, when administered to a susceptible human subject, reproducibly gives rise to a sensation of pain in a joint of such subject in a time period of four to six days. Preferred trigger substances are those known to be safe to administer to a human subject, particularly substances known to be in consumer use or authoritatively regulated for such use under observance of appropriate limitations. Included among such trigger substances are substances commonly added to foods in order to modify their taste; this category of taste-modifiers embraces non-nutritive sweeteners including (but not limited to) saccharin, aspartame, and acesulfame-K as well as flavors and flavor enhancers including (but not limited to) acetoin, anethole, benzaldehyde, cinnamaldehyde, ethyl vanillin, methyl anthranilate, monosodium glutamate, and vanillin; additional categories of trigger substances are preservatives including (but not limited to) phenols such as butylated hydroxyanisole and butylated hydroxytoluene, benzoate compounds such as ammonium benzoate, potassium benzoate, sodium benzoate, and benzoic acid, sulfite compounds such as potassium bisulfite, potassium metabisulfite, sodium bisulfite, sodium metabisulfite, sulfur dioxide, and sulfurous acid, and sorbate compounds such as potassium sorbate, sodium sorbate, and sorbic acid; and pesticides and pesticide residues permitted to be present in or on food including (but not limited to) Captan, Chlorpyrifos, Diazinon, Diquat, Glyphosate, Malathion, Paraquat, pyrethrins, and Thiabendazole and residues resulting from their use.

Trigger substances can also include whole products such as commercially prepared foods in which it may or may not be possible to identify a particular ingredient as responsible for the trigger effect. Such products include many varieties of prepackaged frozen meals as sold in retail markets; whether the trigger substance in such meals be a non-nutritive sweetener contained therein, or a preservative contained therein, or a combination of both, or neither of these, is less important than that a reproducible trigger effect has been observed.

Reproducible pain sensations in a joint noted by a susceptible individual upon ingestion of a trigger substance can occur, for example, in a shoulder, fingers, the lower back, a knee, or a toe.

The quantitity of trigger substance to be administered for pain sensation in a joint to be reproducible is readily determined empirically. For example, a reproducible pain in a shoulder has been noted in a susceptible individual on consuming six prepackaged frozen chicken meals daily for one week on an empty stomach and in the absence of other solid foods.

Agents effective in relieving pain in a joint

In accordance with this invention, any desired agent can be tested for its effectiveness in shortening the duration of pain in a joint produced in a susceptible individual by administration of a trigger substance. The only limitation is the practical requirement of not doing harm to such individual. For that reason, I have sought effective agents principally among substances known to be safe to administer to a human subject, particularly substances known to be nutrients ingested and metabolized by human beings on a daily or at least frequent basis. I have tested many nutrient substances and found effective among these a restricted group of water soluble aminocarboxylic acid compounds at dose levels in the range from 200 to 20000 milligrams. I use the term water soluble to refer to a solubility of at least three grams in 100 ml of water at 25° C.

A preferred group of water soluble aminocarboxylic acid compounds effective according to this invention in relieving pain can be represented by formula (I):

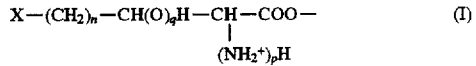

in which X is selected from the group consisting of

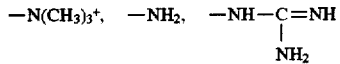

and

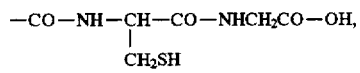

TABLE 1

| # | Name | X | n | p | q |
|---|------|---|---|---|---|
| 1 | 2,5-diaminopentanoic acid | $-NH_2$ | 2 | 1 | 0 |
| 2 | 2,6-diaminohexanoic acid | $-NH_2$ | 3 | 1 | 0 |
| 3 | 2-amino-5-guanidopentanoic acid | $-NH-C(=NH)-NH_2$ | 2 | 1 | 0 |
| 4 | 2-(4-amino-5-carboxypentanoamido)-3-mercapto-N-carboxymethyl-propanoamide | $-CO-NH-CH(CH_2SH)-CO-NHCH_2CO-OH$ | 1 | 1 | 0 |
| 5 | 3-hydroxy-4-trimethylammonio-butanoate | $-N(CH_3)_3^+$ | 1 | 0 | 1 |

Formula (I) and all the effective compounds listed in Table 1 contain an assymetric carbon atom and hence exist in non-superimposable optically active forms (so-called D and L forms) and in racemic mixtures or DL forms. Both D and L forms of the effective compounds and racemic mixtures thereof are contemplated in accordance with this invention.

There is nothing about the structures of the effective compounds of this invention or their known nutrient properties that would have enabled one to predict their effectiveness in relieving pain in a joint in accordance with this invention. This unpredictability is further underscored by the finding that a number of aminocarboxylic acid compounds structurally similar to those effective according to this invention but not structured according to formula (I) are ineffective. In Table 2 following, there are listed a number of aminocarboxylic acid compounds found ineffective in relieving pain when administered after administration of a trigger substance. Some of these compounds can be represented by formula (II)

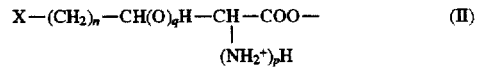

in which the assignments of X and/or n differ from those in formula (I)

TABLE 2

| # | Name | X | n | p | q |
|---|------|---|---|---|---|
| A | 2-aminopropanoic acid | hydrogen | 0 | 1 | 0 |
| B | 2-amino-3-phenylpropanoic acid | phenyl | 0 | 1 | 0 |
| C | 2-amino-3-imidazolyl-propanoic acid | imidazolyl | 0 | 1 | 0 |
| D | 2-aminoacetic acid | not applicable | not applicable | | |
| E | 2-aminopentanedioic acid | —COOH | 2 | 1 | 0 |

While these substances are ineffective in relieving pain in a joint, they are not trigger substances and thus can be present in modest amounts as companion substances to effective agents according to this invention. In this way such substances can contribute to the useful properties of the effective agents by enhancing their speed of action, palatability and/or taste characteristics. When present as companion substances to effective agents their concentration will typically range from 1 to 10 weight percent of the effective agent.

Palatable oral dosage forms

Also in accordance with this invention, a pharmaceutically acceptable carrier can be combined with effective amounts of an effective agent according to this invention to provide a palatable oral dosage form for administering to a person in need of relief of pain in a joint. Accordingly, palatable oral dosage forms according to this invention comprise at least one pharmaceutically acceptable carrier and an effective amount of an effective agent according to this invention. Preferably the effective agent is an aminocarboxylic acid nutrient compound having formula (I). Particularly preferred effective agents are those listed in Table 1.

One preferred palatable oral dosage form according to this invention is a tablet. A particularly preferred tablet according to this invention comprises a high percentage of at least one aminocarboxylic acid nutrient compound having formula (I) and minor amounts of carrier material acting as binder for the tablet. Suitable binder materials include naturally occurring carbohydrates such as cellulose, starch, galactomannan, fructose, lactose, and sucrose; finely divided ingestible mineral substances such as calcium and magnesium carbonates, calcium and magnesium silicates, calcium and magnesium phosphates, alumina hydrates and hydrotalcite; waxy materials such as beeswax, stearin, stearates of calcium, magnesium, and aluminum, microcrystalline wax and paraffin, and mixtures thereof.

Another preferred palatable oral dosage form according to this invention is a capsule. Capsules have the advantage of delivering the effective agent directly to the alimentary canal without being tasted in the mouth. Suitable capsules are commercially available and are typically made of gelatin, but any sufficiently pure water soluble polymer can be used. Preferably the capsule is filled with the pure aminocarboxylic acid nutrient compound having formula (I); alternatively, suspensions of aminocarboxylic acid nutrient compound having formula (I) in a liquid carbohydrate such as corn syrup or honey, or in a lipid such as lecithin or canola oil can be encapsulated.

A further palatable oral dosage form according to this invention comprises an effective amount of an effective agent according to this invention in a liquid carrier such as a fruit flavored drink or a soup, as well as dry concentrates for reconstitution of such drink or soup upon adding water. Preferably, the effective agent is an aminocarboxylic acid nutrient compound having formula (I). Particularly preferred effective agents are those listed in Table 1.

Suitable fruit flavored drinks include natural fruit juices such as pineapple juice, apple juice, grape juice, orange juice, grapefruit juice, cranberry juice, and mixtures thereof; reconstituted juices prepared from water and fruit juice concentrates, and fruit juice drinks containing water and at least 10% of natural fruit juice.

In oral dosage forms according to this invention, the proportions of carrier to effective agent can vary over a broad range in accordance with the kind of carrier selected and the strength desired. Thus the proportion of carrier can be as little as 0.1% by weight, as in a tablet, and as high as 85% or even more, as in a fruit flavored drink or soup.

Tablets in accordance with this invention can be prepared, for example, from 750 milligrams of each of compounds #2, 4, and 5 of Table 1 and 5 milligrams each of stearin, magnesium stearate, and magnesium silicate.

Capsules in accordance with this invention can be prepared, for example, by filling elliptical capsules of 1.5 ml capacity with 500 milligrams of each of compounds #1, 2, 3, 4, and 5 of Table 1.

Fruit flavored drinks in accordance with this invention can be prepared, for example, from 3750 milligrams of each of compounds #1, 2, 3, 4, and 5 of Table 1 and 75 milliliters of commercially available apple-cranberry drink.

Pleasant tasting oral dosage forms

Also in accordance with this invention, a pharmaceutically acceptable carrier can be combined with effective amounts of an effective agent according to this invention and a flavorant to provide a pleasant tasting oral dosage form for administering to a person in need of relief of pain in a joint. Accordingly, pleasant tasting oral dosage forms according to this invention comprise at least one pharmaceutically acceptable carrier, an effective amount of an effective agent according to this invention, and a flavorant. Preferably the effective agent is an aminocarboxylic acid nutrient compound having formula (I). Particularly preferred effective agents are those listed in Table 1.

Preferred flavorants that can be used in a pleasant tasting oral dosage form according to this invention include herbs such as basil, cilantro, dill, oregano, tarragon, and thyme; spices such as cinnamon, clove, ginger, mace, and nutmeg, and essential oils such as oil of lemon, oil of orange, oil of peppermint, and oil of sassafras.

In a particularly preferred pleasant tasting oral dosage form according to this invention, there are present in amounts selected to complement the taste characteristics of each at least one first nutrient compound having the formula

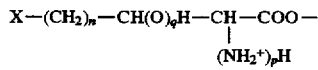

in which X is selected from the group consisting of —NH$_2$, and

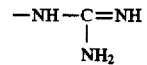

n is two or three, p is one and q is zero.

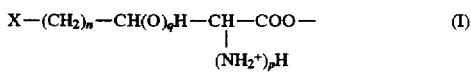

in which X is selected from the group consisting of —N(CH$_3$)$_3$+, and

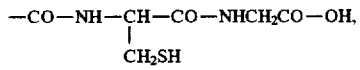

n is zero or one, and p and q are each zero or one, provided that p and q are not both zero and p is zero and q is one only when X is —N(CH₃)₃+.

In such compositions, the taste characteristics of the first nutrient compound and the second nutrient compound interact in such a way as to produce an overall pleasant tasting composition.

Pleasant tasting tablets in accordance with this invention can be prepared, for example, from 750 milligrams of each of compounds #2, 4, and 5 of Table 1, 5 milligrams each of stearin, magnesium stearate, and magnesium silicate, and 10 milligrams of finely powdered cinnamon.

A pleasant tasting fruit flavored drink in accordance with this invention can be prepared, for example, by blending 4500 milligrams of each of compounds #2, 4, and 5 of Table 1, 110 milliliters of commercially available chilled grapefruit juice, and 5 drops oil of orange.

Pleasant tasting tablets containing a first nutrient compound and a second nutrient compound in accordance with this invention can be prepared, for example, from 500 milligrams of each of compounds #2, 4, and 5 of Table 1, 250 milligrams of each of compounds #1 and 3 of Table 1, and 5 milligrams each of stearin, magnesium stearate, and magnesium silicate.

The following Examples are provided to illustrate the invention without intending to limit its scope, which is defined by the appended claims.

EXAMPLE 1

Nine ounce single servings of chicken meals stated to afford 230 calories, 4 grams fat, and 40 milligrams cholesterol as sold frozen and prepackaged in supermarket chains were heated as directed and fed daily for one week on an empty stomach and in the absence of other solid foods to a male human subject known to be susceptible to arthritic pain in joints believed to be associated with the consumption of certain pre-packaged frozen foods. The following observations were recorded

| Trial | Number of servings per day | Extent of pain in the left shoulder after one week |
|---|---|---|
| a | 3 | just noticeable pain when moving |
| b | 6 | dull pain when moving |
| c | 9 | appreciable pain when moving |

The results show that 3 servings per day for a week as given in these trials are clearly sufficient to trigger a marked incidence of pain localized in a joint of this individual, and that the extent of such pain increased with the quantity consumed

EXAMPLE 2

Nine ounce single servings of chicken meals stated to afford 210 calories, 3 grams fat, and 30 milligrams of cholesterol were cooked as directed and fed each day for a week on an empty stomach and in the absence of other solid foods to a female human subject known to be susceptible to arthritic pain in joints believed to be associated with the consumption of certain pre-packaged frozen foods. The following observations were recorded.

| Trial | Servings per day | Extent of pain in the fingers after one week |
|---|---|---|
| a | 2 | no pain |
| b | 4 | just noticeable pain |
| c | 8 | little pain |
| d | 10 | appreciable pain |

The results show that the quantities of substances contained in the meals given in trials b, c, and d are clearly sufficient to trigger a marked incidence of arthritic pain in a joint of this person increasing with the quantity consumed.

EXAMPLES 3–4 and COMPARISON TRIALS 1 and 2

In each of the following trials, a quantity of six servings of prepackaged and frozen chicken as in Example 1 was prepared and served on each day for one week on an empty stomach and in the absence of other solid foods to the same male human subject as in Example 1. At the same time, there was administered a dose of a substance as noted below. The following observations were recorded.

| Example no. | Substance | Dose | Occurrence of shoulder pain after one week |
|---|---|---|---|
| 3 | Blend of substances from Table 1 | 2000 mg | slight pain |
| 4 | ditto | 4000 mg | no pain |
| Comparison 1 | none | | steady dull pain |
| Comparison 2 | blend of substances from table 2 | 4000 | steady dull pain |

The results show the blend of substances shown in Examples 3 and 4 was an effective agent according to this invention in diminishing or preventing the incidence of pain in a joint triggered by consumption of the prepackaged frozen meal in accordance with a method of this invention. The results also show that compounds of Table 2 with structural similarity to those effective according to this invention but differing in the assignments of X and/or n in the formula were ineffective.

I claim:

1. The method of determining the effectiveness of a nutrient agent for relieving pain in a joint of a person in need of such relief, comprising the steps of
   a) administering to a susceptible person a quantity of a trigger substance which is selected from the group consisting of taste modifiers, preservatives, pesticides and pesticide residues permitted to be present in or on food, and prepackaged frozen meals, and which is reproducibly effective in producing within a period of not more than ten days the occurrence of pain in a joint of said person lasting for at least one week in the absence of treatment,
   b) administering to said person receiving said quantity of trigger substance a predetermined quantity of a nutrient agent having the formula

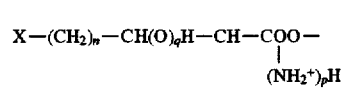

in which X is selected from the group consisting of —N(CH₃)₃+, —NH₂,

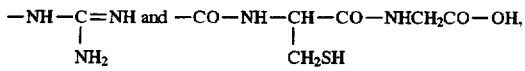

n is zero, one, two or three, and p and q are each zero or one, provided that p and q are not both zero and p is zero and q is one only when X is —N(CH$_3$)$_3$+, whose effectiveness in relieving pain in a joint is to be determined, c) measuring the time required for relief of pain in a joint of the person upon administering said agent, and d) comparing the time required for relief of said pain with and without the administration of said nutrient agent.

2. The method of claim 1 in which said trigger substance comprises a prepackaged frozen meal.

3. The method of claim 1 in which administration of said trigger substance and administration of said agent are substantially simultaneous.

4. The method of claim 1 in which said agent is administered prior to exposure to said trigger substance.

5. The method of claim 1 in which said agent is administered subsequent to exposure to said trigger substance.

6. The method of relieving pain caused by a substance selected from the group consisting of taste modifiers, preservatives, pesticides and pesticide residues permitted to be present in or on food, and prepackaged frozen meals, in a joint of a person in need of such relief, comprising the administration to such person of a nutrient substance having the formula

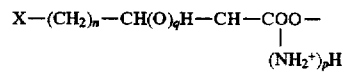

in which X is selected from the group consisting of —N(CH$_3$)$_3$+, —NH$_2$,

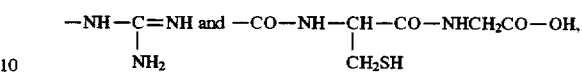

n is zero, one, two or three, and p and q are each zero or one, provided that p and q are not both zero and p is zero and q is one only when X is —N(CH$_3$)$_3$+.

7. The method of claim 6 in which X is —NH$_2$ and n is two.

8. The method of claim 6 in which X is

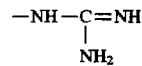

and n is two.

9. The method of claim 6 in which X is

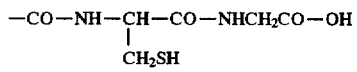

and n is one.

10. The method of claim 6 in which X is —N(CH$_3$)$_3$+, n is zero, p is zero, and q is one.

* * * * *